United States Patent
Vargas et al.

(10) Patent No.: US 8,956,683 B2
(45) Date of Patent: Feb. 17, 2015

(54) CHEMICAL VAPOR INFILTRATION APPARATUS AND PROCESS

(75) Inventors: Joseph R. Vargas, Garnerville, NY (US); Steven J. Seelman, Montclair, NJ (US); David B. Roberts, Parsippany, NJ (US)

(73) Assignee: Zimmer, Inc., Warsaw, IN (US)

( * ) Notice: Subject to any disclaimer, the term of this patent is extended or adjusted under 35 U.S.C. 154(b) by 205 days.

(21) Appl. No.: 13/523,073

(22) Filed: Jun. 14, 2012

(65) Prior Publication Data

US 2012/0321779 A1    Dec. 20, 2012

Related U.S. Application Data

(60) Provisional application No. 61/497,803, filed on Jun. 16, 2011.

(51) Int. Cl.

| C23C 16/00 | (2006.01) |
| C23C 16/00 | (2006.01) |
| B05D 3/00 | (2006.01) |
| A61F 2/28 | (2006.01) |
| C23C 16/44 | (2006.01) |
| C23C 16/04 | (2006.01) |
| C23C 16/08 | (2006.01) |
| C23C 16/455 | (2006.01) |
| C23C 16/458 | (2006.01) |
| A61F 2/30 | (2006.01) |

(52) U.S. Cl.
CPC ........... C23C 16/4405 (2013.01); C23C 16/045 (2013.01); C23C 16/08 (2013.01); C23C 16/45557 (2013.01); C23C 16/458 (2013.01); A61F 2/3094 (2013.01); A61F 2002/30981 (2013.01)
USPC .................... 427/2.26; 427/2.24; 427/255.12; 623/23.51; 118/715

(58) Field of Classification Search
CPC ........ A61F 2/28; A61F 2/30767; B22F 3/114
USPC .................. 427/2.24, 2.26, 255.12; 623/23.51
See application file for complete search history.

(56) References Cited

U.S. PATENT DOCUMENTS

| 4,138,512 A | 2/1979 | Glaski |
| RE30,626 E | 5/1981 | Kaplan |

(Continued)

FOREIGN PATENT DOCUMENTS

| EP | 1927325 A1 | 6/2008 |
| WO | WO99/56800 A1 | 11/1999 |

(Continued)

OTHER PUBLICATIONS

"International Application Serial No. PCT/US2012/042402, International Preliminary Report on Patentability mailed Jan. 3, 2014", 12 pgs.

(Continued)

*Primary Examiner* — Cachet Sellman
(74) *Attorney, Agent, or Firm* — Schwegman Lundberg & Woessner, P.A.

(57) ABSTRACT

The present invention relates to improvements in chemical vapor infiltration processes and devices for depositing a biocompatible material onto a porous substrate to form an orthopedic implant. The substrate may be formed of reticulated vitreous foam and coated with tantalum, niobium, tungsten, or other biocompatible materials.

25 Claims, 13 Drawing Sheets

(56) References Cited

U.S. PATENT DOCUMENTS

| | | | |
|---|---|---|---|
| 4,699,082 A | 10/1987 | Hakim | |
| 4,821,674 A | 4/1989 | deBoer et al. | |
| 4,996,942 A | 3/1991 | deBoer et al. | |
| 5,102,694 A | 4/1992 | Taylor et al. | |
| 5,154,970 A | 10/1992 | Kaplan et al. | |
| 5,169,685 A | 12/1992 | Woodruff et al. | |
| 5,198,034 A | 3/1993 | deBoer et al. | |
| 5,282,861 A * | 2/1994 | Kaplan | 623/23.51 |
| 5,283,109 A | 2/1994 | Kaplan et al. | |
| 5,306,666 A | 4/1994 | Izumi | |
| 5,374,315 A | 12/1994 | deBoer et al. | |
| 5,427,620 A | 6/1995 | deBoer et al. | |
| 5,427,631 A | 6/1995 | Johnsson et al. | |
| 5,443,515 A | 8/1995 | Cohen et al. | |
| 5,443,647 A | 8/1995 | Aucoin et al. | |
| 5,574,247 A | 11/1996 | Nishitani et al. | |
| 5,577,263 A | 11/1996 | West | |
| 5,716,495 A * | 2/1998 | Butterbaugh et al. | 438/708 |
| 5,755,809 A | 5/1998 | Cohen et al. | |
| 5,780,157 A | 7/1998 | Tuffias et al. | |
| 5,840,366 A | 11/1998 | Mizuno et al. | |
| 5,849,092 A * | 12/1998 | Xi et al. | 134/1.1 |
| 5,874,131 A | 2/1999 | Vaartstra et al. | |
| 5,876,793 A | 3/1999 | Sherman et al. | |
| 5,902,407 A | 5/1999 | deBoer et al. | |
| 5,919,531 A | 7/1999 | Arkles et al. | |
| 6,063,442 A | 5/2000 | Cohen et al. | |
| 6,083,560 A | 7/2000 | Fisher et al. | |
| 6,352,594 B2 | 3/2002 | Cook et al. | |
| 6,641,918 B1 | 11/2003 | Sherman et al. | |
| 6,770,146 B2 | 8/2004 | Koren et al. | |
| 6,797,340 B2 | 9/2004 | Fang et al. | |
| 6,833,161 B2 | 12/2004 | Wang et al. | |
| 6,878,395 B2 | 4/2005 | Kaeppeler | |
| 6,949,273 B2 | 9/2005 | Sharan | |
| 7,368,018 B2 | 5/2008 | Yamaguchi | |
| 7,374,941 B2 | 5/2008 | Bondestam et al. | |
| 7,479,301 B2 | 1/2009 | Eriksen | |
| 7,485,340 B2 | 2/2009 | Elers et al. | |
| 7,601,393 B2 | 10/2009 | Chiang et al. | |
| 2002/0162500 A1 | 11/2002 | Hong et al. | |
| 2002/0197403 A1 | 12/2002 | Arkles et al. | |
| 2005/0011457 A1 | 1/2005 | Chiang et al. | |
| 2006/0110534 A1 | 5/2006 | Hwang et al. | |
| 2007/0061006 A1 | 3/2007 | Desatnik | |
| 2008/0096369 A1 | 4/2008 | Strzyzewski et al. | |
| 2008/0124462 A1 | 5/2008 | Waghray et al. | |
| 2008/0296660 A1 | 12/2008 | Park et al. | |
| 2008/0317954 A1 | 12/2008 | Lu et al. | |
| 2009/0056630 A1 | 3/2009 | Hester et al. | |
| 2009/0107404 A1 | 4/2009 | Ogliari et al. | |
| 2009/0205563 A1 | 8/2009 | Arena et al. | |
| 2009/0214786 A1 | 8/2009 | Chang et al. | |
| 2009/0232983 A1 | 9/2009 | Ammerlaan et al. | |
| 2009/0288604 A1 | 11/2009 | Kim et al. | |
| 2010/0094430 A1 * | 4/2010 | Krumdieck | 623/23.5 |
| 2011/0033631 A1 | 2/2011 | Malshe et al. | |

FOREIGN PATENT DOCUMENTS

| | | |
|---|---|---|
| WO | WO-2012174207 A2 | 12/2012 |
| WO | WO-2012174207 A3 | 12/2012 |

OTHER PUBLICATIONS

"International Application Serial No. PCT/US2012/042402, International Search Report mailed Jan. 28, 2013", 6 pgs.

"International Application Serial No. PCT/US2012/042402, Invitation to Pay Additional Fees mailed Sep. 5, 2012", 5 pgs.

"International Application Serial No. PCT/US2012/042402, Written Opinion mailed Jan. 28, 2013", 11 pgs.

"Experimental and clinical performance of porous tantalum in orthopedic surgery", Brett Levin et al., Biomaterials Bolumn 27, Issue 27, Sep. 2006, pp. 4671-4681—Abstract.

"Chemical Vapor Deposition by Pulsed Ultrasonic Direct Injection of Liquid Precursors Produces Versatile Method for Creation of thin Film Circuits and Devices", Mark Leiby, Materials Research Society, URL: http://www.mrs.org/s_mrs/sec_subscribe.asp?CID=2505&DID=135969&action=detail.

Formability of Porous Tantalum Sheet-Metal, Nebosky et al., IOP Publishing 2009, Materials Science and Engineering 4 (2009).

RD52148A, Sep. 10, 2007, Unknown.

* cited by examiner

CHEMICAL VAPOR INFILTRATION APPARATUS AND PROCESS

CROSS REFERENCE TO RELATED APPLICATION

This application claims priority from U.S. Provisional Patent Application Serial No. 61/497,803, filed Jun. 16, 2011, the disclosure of which is hereby expressly incorporated by reference herein in its entirety.

FIELD OF THE DISCLOSURE

The present invention relates to improvements in chemical vapor infiltration (CVI) methods. In particular, the present invention relates to improvements in a CVI apparatus and process for depositing a biocompatible material onto a porous substrate.

BACKGROUND

Orthopedic implants may be constructed of, or coated with, porous biomaterial to encourage bone growth into the implant. One example of such material is a porous tantalum metal or metal alloy produced using Trabecular Metal™ technology generally available from Zimmer, Inc., of Warsaw, Ind. Trabecular Metal™ is a trademark of Zimmer, Inc. This porous material may be formed of a reticulated vitreous carbon (RVC) bone-like substrate which is infiltrated and coated with a biocompatible material, such as tantalum, in the manner disclosed in U.S. Pat. No. 5,282,861 to Kaplan, the disclosure of which is expressly incorporated herein by reference. The resulting coated material is lightweight, strong, and has an open-cell structure that is similar to the structure of natural cancellous bone, thereby providing a matrix into which cancellous bone may grow to fix the orthopedic implant to the patient's bone.

The starting material for the porous tantalum material is an open-cell polymer foam block or sheet. This polymer foam material is converted into the RVC substrate by first impregnating the polymer foam with a carbonaceous resin and then heating the impregnated foam to a suitable pyrolysis temperature, on the order of 800° C.-2000° C., to convert the polymer foam and any carbonaceous resin into vitreous carbon having individual carbon foam ligaments. The RVC may be shaped into the final form of the orthopedic implant using machining or other shaping techniques. Using CVI, a biocompatible material, such as tantalum, niobium, tungsten, or alloys thereof, may then be coated onto the RVC substrates in a heated reaction chamber. For example, in order to deposit tantalum onto the RVC substrates, solid tantalum metal (Ta) is heated to react with chlorine gas ($Cl_2$) to form tantalum chloride gas, such as tantalum pentachloride ($TaCl_5$), for example. The tantalum chloride gas flows into the reaction chamber and is mixed with hydrogen gas ($H_2$). Upon contact with the heated surface of the substrates, as shown in Equation 1 below, tantalum metal deposits onto the substrates in a thin film over the individual ligaments of the substrates and the hydrogen and chlorine gases react to form hydrogen chloride gas (HCl), which is exhausted from the reaction chamber:

$$TaCl_5 + 5/2 H_2 \rightarrow Ta + 5\ HCl \qquad \text{Equation 1}$$

This CVI cycle may be repeated, with the positions of the substrates in the reaction chamber varied, until the substrates are uniformly coated with tantalum. Following each CVI cycle, the hydrogen chloride gas byproduct and any non-converted tantalum chloride gas may react with water and aqueous sodium hydroxide solution to precipitate tantalum oxide, sodium chloride, and water, as is shown in Equation 2:

$$2\ HCl_{(g)} + 2\ TaCl_{5(g)} + H_2O_{(l)} + 12\ NaOH_{(aq)} \rightarrow Ta_2O_{5(s)} + 12\ NaCl_{(aq)} + 8\ H_2O_{(l)} \qquad \text{Equation 2}$$

SUMMARY

The present disclosure relates to improvements in a CVI apparatus and process for depositing a biocompatible material onto a porous substrate to form an orthopedic implant. The substrate may be formed of RVC foam and coated with tantalum, niobium, tungsten, or other biocompatible materials.

In one exemplary embodiment, the CVI apparatus includes a reactor design in which the tantalum source is supported below the substrates.

In another exemplary embodiment, the apparatus includes a reactor design with an adjustable vacuum.

In yet another exemplary embodiment, the apparatus includes a reactor design in which the gas flow is homogenized within a deposition chamber of the apparatus.

In still yet another exemplary embodiment, the apparatus includes a reactor design with a variable temperature profile.

In a further exemplary embodiment, the apparatus includes a reactor designed to rapidly cool the reaction chamber after a CVI cycle.

In a still further exemplary embodiment, the apparatus includes a reactor designed to self-clean after a CVI cycle.

It is within the scope of the present disclosure that a single apparatus may include multiple or all of the above-described features. For example, a single apparatus may include a tantalum source supported below the substrates, an adjustable vacuum, a homogenized gas flow, a variable temperature profile, a rapid cooling cycle, and a self-cleaning cycle.

According to an exemplary embodiment of the present disclosure, a method is provided for operating a chemical vapor infiltration apparatus to produce an orthopedic implant. The method includes the steps of: placing a porous substrate into a reaction chamber of the chemical vapor infiltration apparatus; exposing the porous substrate to a first gas and a second gas in the reaction chamber, the first and second gases reacting and depositing a biocompatible metal onto the porous substrate to produce the orthopedic implant; and varying a vacuum level in the reaction chamber during the exposing step.

According to another exemplary embodiment of the present disclosure, a chemical vapor infiltration apparatus is provided for producing an orthopedic implant. The apparatus includes: a reaction chamber having a first gas input for receiving a first gas and a second gas input for receiving a second gas, the first and second gases reacting to form a biocompatible metal; a shelving unit in the reaction chamber that is sized to hold a plurality of porous substrates in a stacked arrangement, the biocompatible metal depositing onto the plurality of porous substrates; and an actuator configured to rotate the shelving unit and the plurality of porous substrates on the shelving unit relative to the reaction chamber.

According to yet another exemplary embodiment of the present disclosure, a method is provided for operating a chemical vapor infiltration apparatus to produce an orthopedic implant. The method includes the steps of: placing a porous substrate into a reaction chamber of the chemical vapor infiltration apparatus; depositing a first portion of a biocompatible metal onto the porous substrate to produce the orthopedic implant, and a second portion of the biocompatible metal onto the reaction chamber; and cleaning the reaction chamber by heating the reaction chamber and injecting a chlorine stripping gas into the heated reaction chamber, the chlorine stripping gas reacting with the second portion of the biocompatible metal to remove the second portion of the biocompatible metal from the reaction chamber.

BRIEF DESCRIPTION OF THE DRAWINGS

The above-mentioned and other features and advantages of this disclosure, and the manner of obtaining them, will become more apparent and the invention itself will be better understood by reference to the following description of embodiments of the disclosure taken in conjunction with the accompanying drawings.

Corresponding reference characters indicate corresponding parts throughout the several views. The exemplifications set out herein illustrate exemplary embodiments of the disclosure and such exemplifications are not to be construed as limiting the scope of the disclosure in any manner.

DETAILED DESCRIPTION

Figure 2:
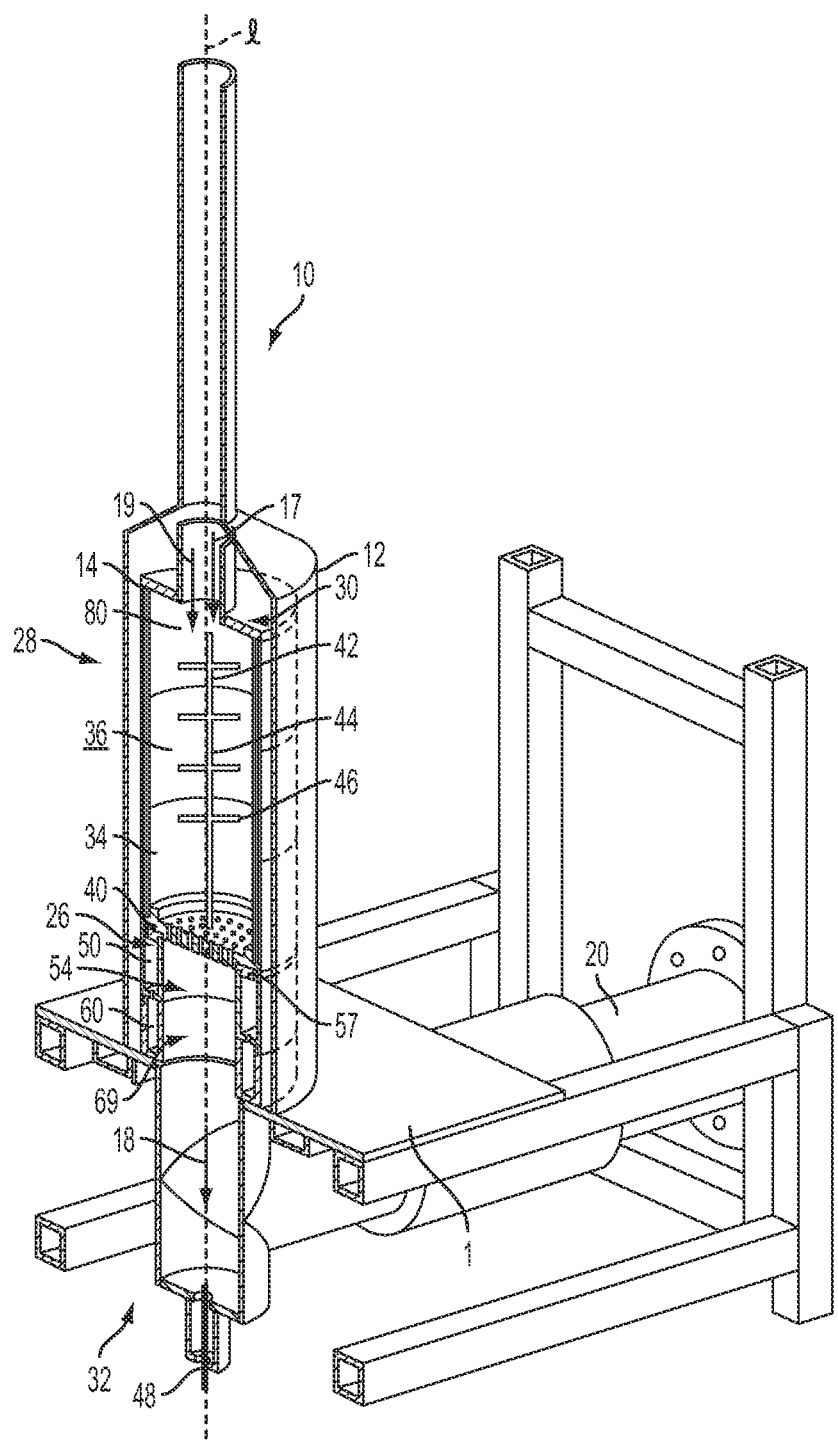
FIG. 2 is a cross-sectional view of an apparatus for depositing tantalum onto a RVC foam substrate using CVI.
Figure 3:
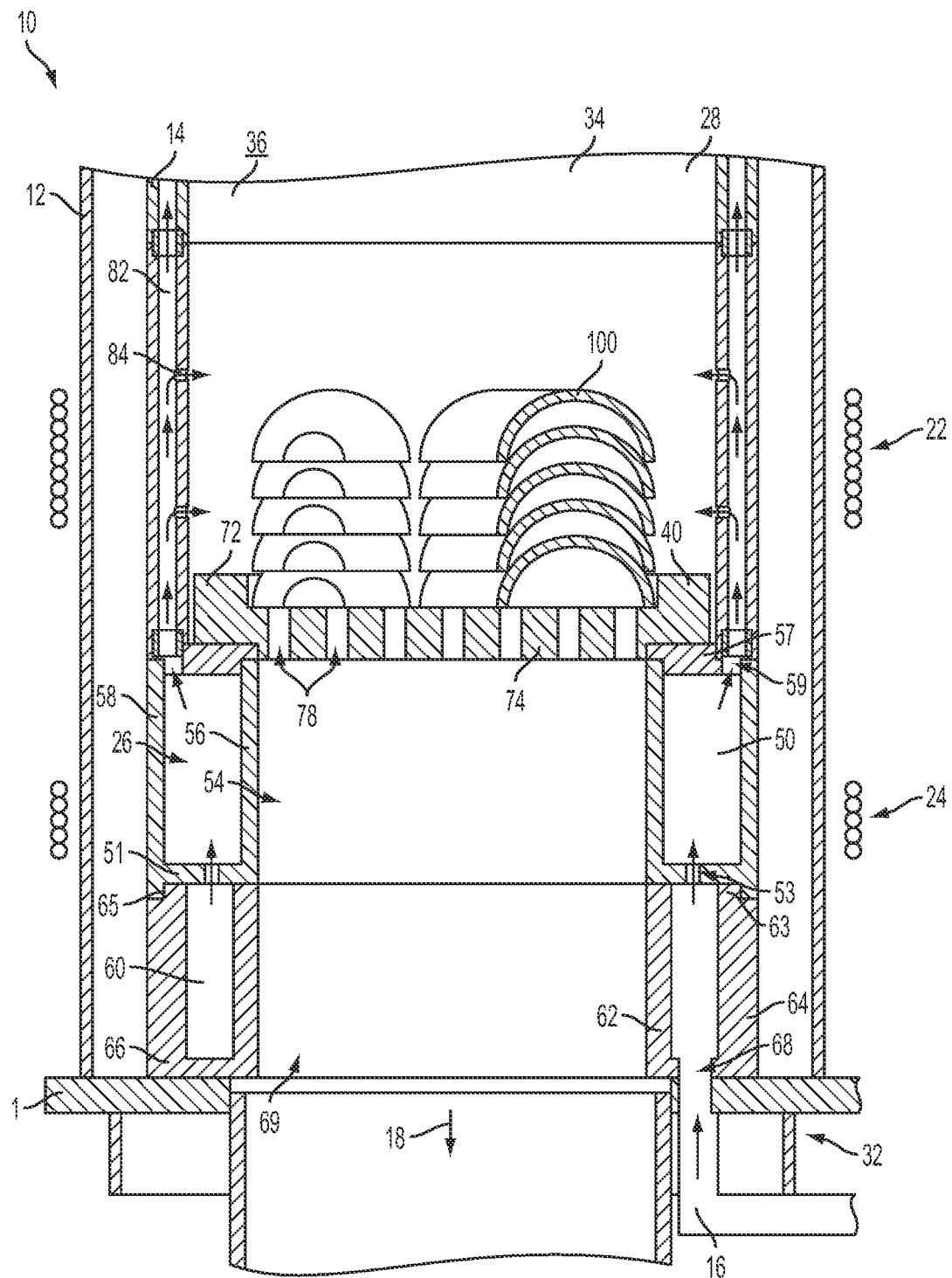
FIG. 3 is a cross-sectional view of a lower end of the apparatus of FIG. 2.

Exemplary methods, processing steps, and devices for improving CVI, alternatively referred to as chemical vapor deposition (CVD), of a biocompatible material onto porous substrates 100 (FIG. 3) are provided herein. Referring to FIGS. 2 and 3, an illustrative embodiment CVI apparatus 10 is used to deposit tantalum onto one or more substrates 100, which are illustratively comprised of RVC foam. Other biocompatible materials, such as niobium and tungsten, may be deposited onto the substrates 100 or other similar porous materials.

FIG. 2 is a schematic view of the apparatus 10, and it is understood that the design of the apparatus 10 may vary. The apparatus 10 is positioned on a table 1 and includes a housing 12, illustratively made of glass, that surrounds an internal reaction chamber 14, which is made of graphite or other conductive materials. The apparatus 10 includes a chlorine gas ($Cl_2$) input 16, shown in FIG. 3, as well as a hydrogen gas ($H_2$) input 17, and an air input 19 into the reaction chamber 14. The apparatus 10 also includes an exhaust gas output 18 from the reaction chamber 14 and a vacuum system 20. Additionally, the reaction chamber 14 is operably coupled to at least one heat source, such as induction coils 22, 24 (FIG. 3). Within the reaction chamber 14, the apparatus 10 includes a heated chlorination chamber 26 and a heated deposition chamber 28 or furnace. A supply of tantalum or another biocompatible metal is associated with the chlorination chamber 26 and the substrates 100 are located within the deposition chamber 28. The substrates 100 may include a bulk quantity of material in the form of a block or sheet; however, as shown in FIG. 3, exemplary substrates 100 include a plurality of individual components that have been formed into the shape of orthopedic implants, such as acetabular cups.

The illustrative reaction chamber 14 is defined by an upper end 30, a lower end 32, and a substantially cylindrical side wall 34 extending therebetween and along a longitudinal axis l. An inner surface 36 of the side wall 34 defines a longitudinal length of the reaction chamber 14. The substrates 100 are positioned within the deposition chamber 28 and may be supported on an internal structure, such as a plate 40 or shelving unit 42. The plate 40 and shelving unit 42 may be configured to support the substrates 100 in a stacked arrangement, as shown in FIG. 3. As is shown in FIG. 2, the shelving unit 42 may resemble a tree and includes a plurality of shelves 46 extending radially outwardly from a central post 44 to support the substrates 100. Further details of the plate 40 will be explained below. The post 44 extends along the longitudinal length of the deposition chamber 28.

The CVI process and apparatus 10 may be configured to facilitate adjustment of certain processing parameters, such as time, temperature, gas flow rates, and vacuum levels. To determine the effect of varying these parameters, and in order to improve the CVI process, deposition efficiency and weight variance are measured. Deposition efficiency is a process output that determines the percentage of tantalum that successfully deposits onto the substrates 100 during one CVI cycle, as is shown in Equation 3 below. The tantalum source is the amount of tantalum that is converted from the solid to gaseous state and flows from the chlorination chamber 26 to the deposition chamber 28. Deposition efficiency compares the amount of tantalum source to the amount of tantalum actually deposited on a given substrate (i.e., the amount of gaseous tantalum in the deposition chamber 28 that reacts with a given substrate 100 and deposits thereon).

$$\text{Deposition Efficiency} = (Ta_{deposited}/Ta_{source}) \qquad \text{Equation 3}$$

It should be noted that increasing the deposition efficiency is not equivalent to increasing the deposition rate. Deposition rate, in contrast to deposition efficiency, is the rate at which tantalum is deposited onto the substrates 100. If tantalum is deposited onto the substrates 100 too rapidly, the tantalum may not effectively infiltrate the pores (not shown) of the substrates 100 and therefore may be thicker and non-uniform on the exterior of the substrates 100 but thinner on the internal ligaments of the substrates 100.

Weight variance (WV) is a process output measuring the variance, or standard deviation squared, in the weight of one of the substrates 100 after one CVI cycle. To determine the change in weight variance, the weight variance of an individual substrate 100 after one CVI cycle is subtracted from the weight variance measured for that same substrate 100 in the subsequent CVI cycle, as is shown in Equation 4:

$$\Delta WV = WV_{after} - WV_{before} \qquad \text{Equation 4}$$

Deposition efficiency and weight variance affect the number of CVI cycles that must be performed in order to uniformly coat each substrate component 100. Therefore, by decreasing the weight variance and increasing the deposition efficiency, the overall time required to produce a porous tantalum implant decreases because fewer CVI cycles are needed to form a uniform tantalum coating on the substrates 100. Additionally, improvements in weight variance and deposition efficiency may eliminate some processing steps, such as rearranging the substrates 100 after each CVI cycle in order to deposit a uniform tantalum coating onto the substrates 100.

Deposition efficiency and weight variance are used to quantify the effectiveness of the improvements illustrated in the exemplary embodiments detailed hereinafter. In one exemplary embodiment, the CVI apparatus 10 includes a reactor design in which the tantalum source is supported below the substrates 100. In another illustrative embodiment, the apparatus 10 includes a reactor design with an adjustable vacuum 20. In yet another illustrative embodiment, the apparatus 10 includes a reactor design in which the gas flow is homogenized within the deposition chamber 28. A further illustrative embodiment of the apparatus 10 includes a reactor design with a variable temperature profile in the deposition chamber 28. Additionally, another illustrative embodiment of the apparatus 10 includes a reactor design configured to rapidly cool the reaction chamber 14 after a CVI cycle.

1. Tantalum Pot Location

Figure 1:
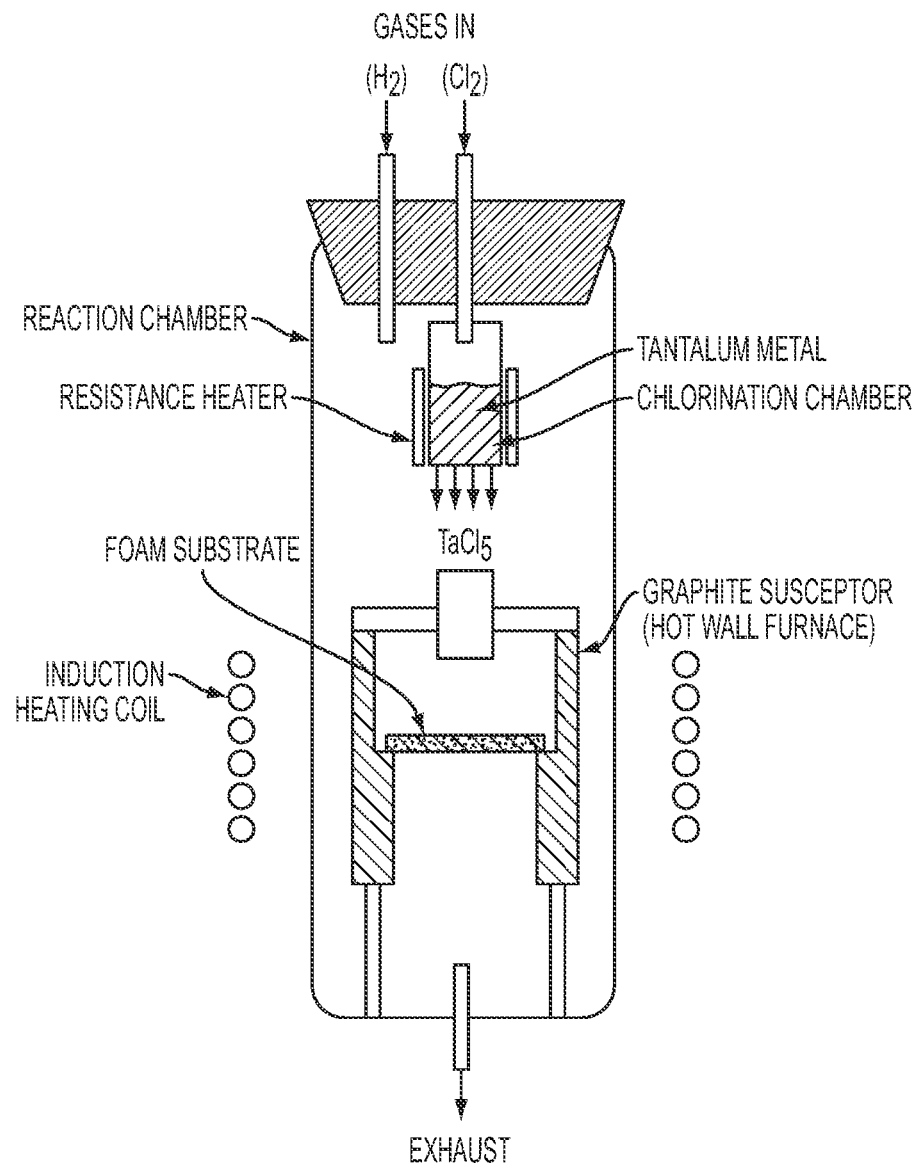
FIG. 1 is a prior art reaction chamber for CVI.

As shown in FIG. 1, it is known to place solid tantalum, in the form of nuggets or other scrap tantalum, within a holding device of a chlorination chamber with the holding device positioned above the substrates. As such, chlorine gas and solid tantalum react within the heated chlorination chamber to form gaseous tantalum chloride, which flows in a downward direction toward the substrate. However, one potential problem with this arrangement is that the varying temperatures inside the reaction chamber may eventually cause the holding device to break, thereby dropping the solid tantalum onto the substrates and necessitating termination of the process and disposal of the substrates.

As is detailed in FIGS. 2-8, to improve CVI of tantalum onto the substrates 100, the illustrative internal reaction chamber 14 includes an internal tantalum pot 50 located below the substrates 100. The illustrative internal tantalum pot 50 is positioned near the lower end 32 of the reaction chamber 14 and contains pieces of solid tantalum. Specifically, the pot 50 supports a predetermined weight of tantalum. In this way, if the tantalum pot 50 cracks, breaks, or otherwise fails during a CVI cycle, the substrates 100 are not affected.

Figure 4A:
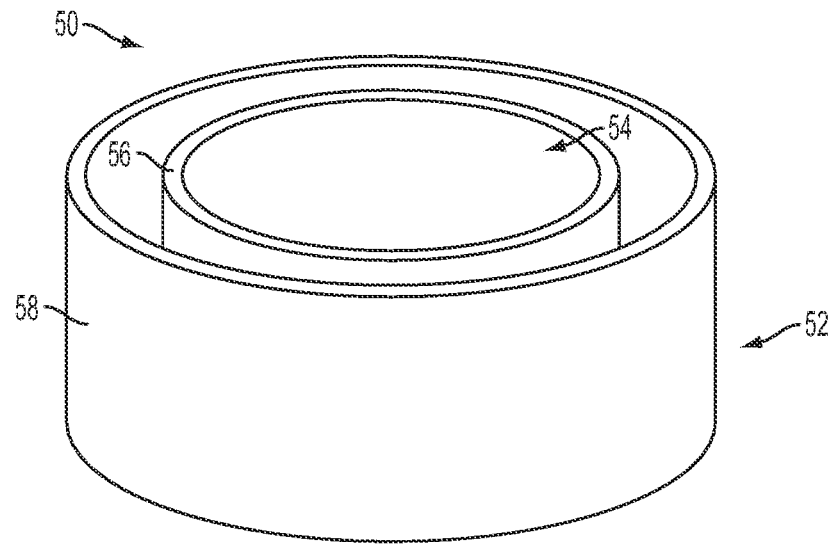
FIGS. 4A and 4B are detailed views of an internal tantalum pot of the apparatus of FIG. 2.
Figure 4B:
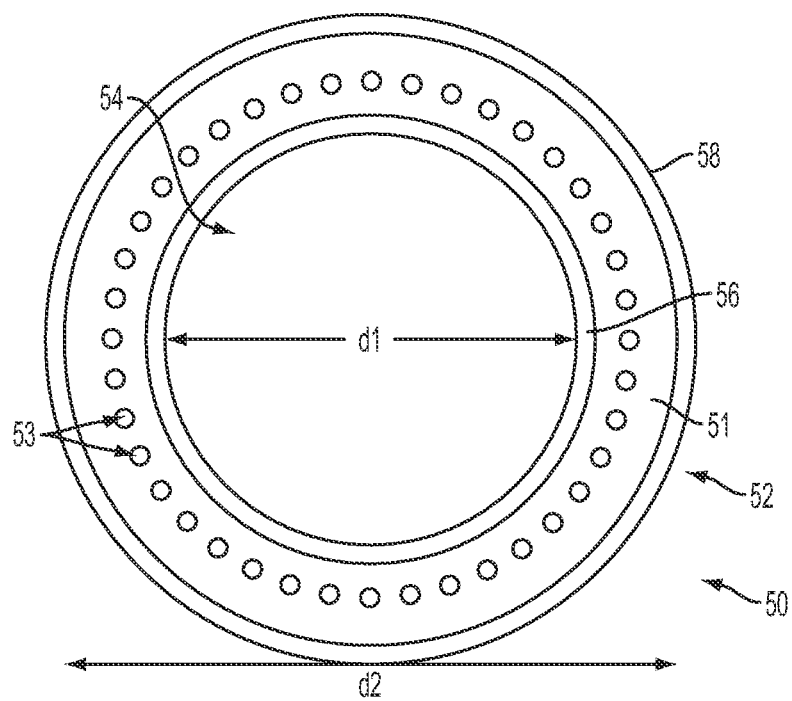

With reference to FIGS. 4A and 4B, the illustrative tantalum pot 50 is an annular ring 52 with an open center portion 54. In particular, the pot 50 includes an internal wall 56 that defines an inner diameter $d_1$ and an outer wall 58 that defines an outer diameter $d_2$. The pot 50 further includes a bottom surface 51 to support the tantalum within the pot 50. The bottom surface 51 of the pot 50 includes a plurality of gas ports 53 through which chlorine gas flows into the pot 50 and over and around the solid tantalum to form tantalum chloride gas.

The chlorine gas input 16 is illustratively supplied from below the tantalum pot 50 and flows in an upward direction into the pot 50 to form tantalum chloride in the chlorination chamber 26. The tantalum chloride also flows in an upward direction to exit the chlorination chamber 26 and enter the deposition chamber 28. Conversely, the hydrogen gas and air flow downwardly into the deposition chamber 28 via the hydrogen gas input 17 and the air input 19, respectively, which are positioned near the upper end 30 of the reaction chamber 14. Therefore, the upward flow of tantalum chloride gas mixes with the downward flow of hydrogen gas and air in the deposition chamber 28 and then reacts to deposit tantalum onto the substrates 100. The exhaust outlet 18 is provided near the lower end 32 of the reaction chamber 14 in order for hydrogen chloride byproduct and excess reactant gases to exit the reaction chamber 14.

Figure 5:
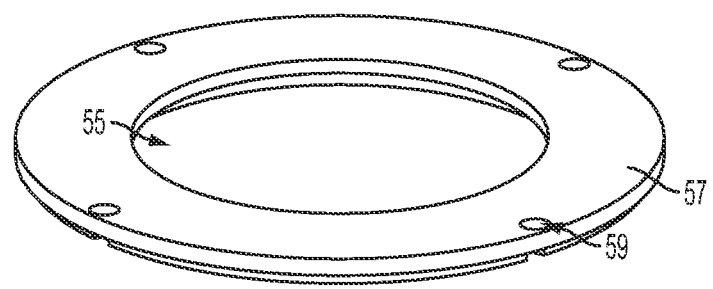
FIG. 5 is a detailed view of a lid that couples to the tantalum pot of FIGS. 4A-4B.

Referring to FIG. 5, the pot 50 also may include a lid 57 having a plurality of gas flow ports 59 to facilitate the flow of chlorine gas and/or tantalum chloride gas. Therefore, the flow ports 59 provide a passageway for gaseous tantalum chloride to exit the chlorination chamber 26 and enter the deposition chamber 28. The shape of the lid 57 substantially corresponds to the respective inner and outer walls 56, 58 of the pot 50 and also includes an open center portion 55.

Figure 6A:
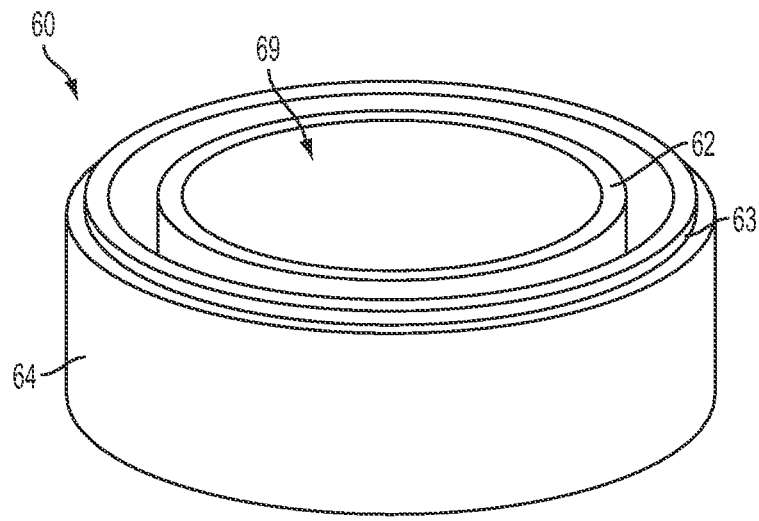
FIGS. 6A and 6B are detailed views of a manifold positioned below the apparatus of FIG. 2.
Figure 6B:
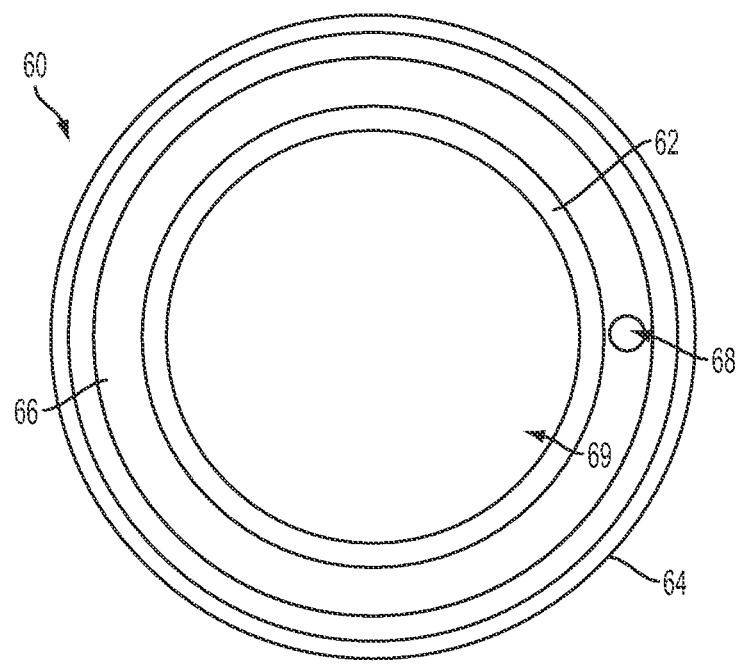

Referring to FIGS. 6A and 6B, the reaction chamber 14 may include a manifold 60 coupled to the tantalum pot 50 near the lower end 32 of the reaction chamber 14. The manifold 60 also is shaped as an annular ring and includes an inner wall 62 and an outer wall 64 that are positioned directly below the inner and outer walls 56, 58, respectively, of the pot 50. The outer wall 64 of the manifold 60 may include a step 63 that couples with a corresponding step 65 (FIG. 3) on the outer wall 58 of the tantalum pot 50. Likewise, the manifold 60 includes a bottom surface 66 having at least one gas flow port 68 to facilitate the flow and distribution of chlorine gas from the chlorine gas input 16 to the tantalum pot 50. For example, after chlorine gas enters the gas flow port 68 of the manifold 60, the chlorine gas may flow throughout the manifold 60 for even distribution into the tantalum pot 50 via the plurality of gas ports 53, including those gas ports 53 that are spaced away from the chlorine gas input 16 and the gas flow port 68. Also, the manifold 60 includes an open center portion 69 which is aligned with open center portions 54, 55 of the tantalum pot 50 and the lid 57, respectively, and through which gaseous byproducts exit the reaction chamber 14 via the exhaust output 18.

Figure 7:
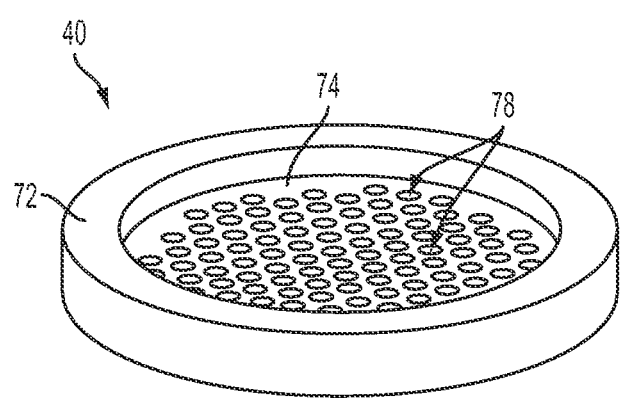
FIG. 7 is a detailed view of a plate that supports the substrate within the apparatus of FIG. 2.

Referring to FIGS. 2, 3, and 7, the lid 57 may extend into the deposition chamber 28 and couples with the plate 40. The plate 40 includes an outer ledge 72 and a recess 74 extending below the outer ledge 72 to support the substrates 100. Illustratively, the recess 74 is received within the open center portion 55 of the lid 57, while the outer ledge 72 is radially supported by the lid 57. The recess 74 includes a plurality of flow ports 78 that facilitate gas flow out of the reaction chamber 14 via exhaust output 18.

Figure 8:
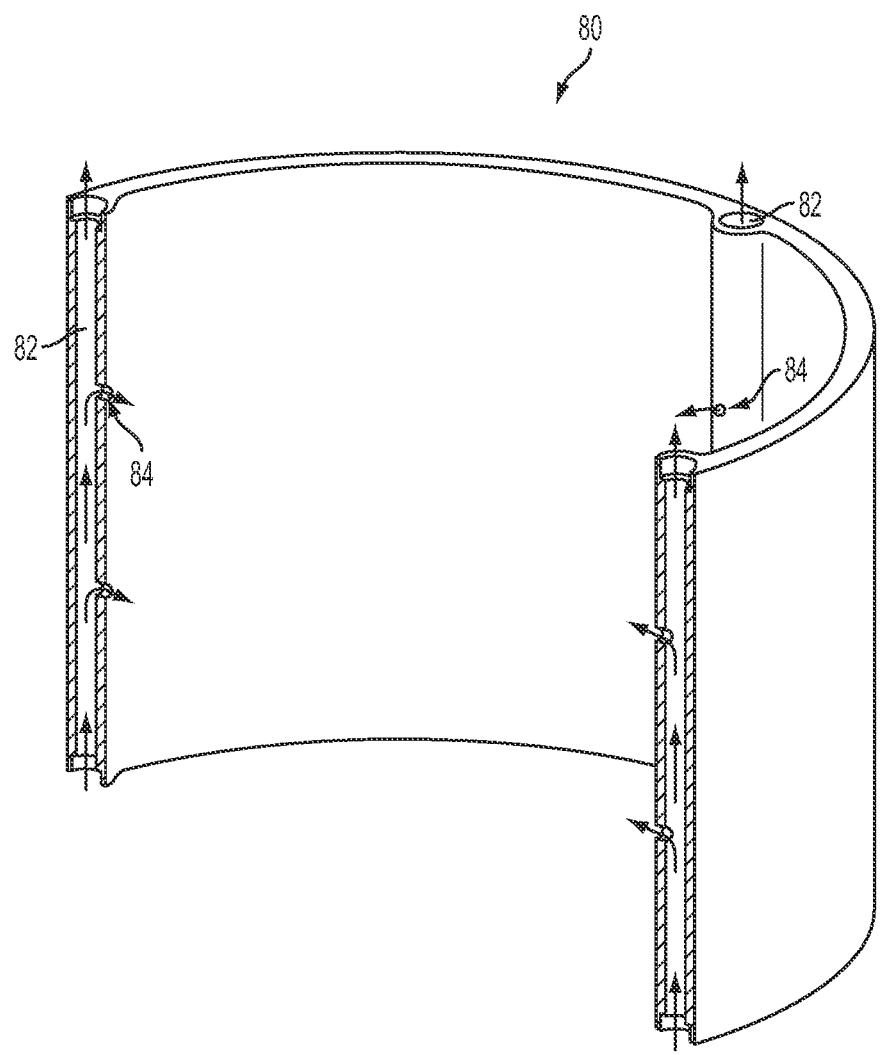
FIG. 8 is a cross-sectional view of a cylindrical wall of the apparatus of FIG. 2.

Referring to FIGS. 2 and 8, the side wall 34 of the reaction chamber 14 may be comprised of a plurality of cylindrical sections 80 configured in a stacked arrangement to define the deposition chamber 28. The section 80 positioned adjacent to the chlorination chamber 26 couples with the lid 57, while the other sections 80 couple with each other. Each section 80 may be formed of graphite material or other conductive materials to facilitate heating by the induction coil 22 (FIG. 3). Each section 80 may also include a plurality of tubular members 82, which extend vertically along the length of the section 80 and are positioned at spaced intervals around the circumference of the section 80. Illustratively, the tubular members 82 are radially positioned around the section 80 at 90° intervals, however, this distance may vary. For example, the tubular members 82 also may be spaced apart by 45° or 180°, or by other angles or increments. Each tubular member 82 aligns with adjacent tubular members 82 in other sections 80 to provide a pathway for gases to flow along the longitudinal length of the reaction chamber 14. Additionally, each tubular member 82 includes at least one gas flow port 84 for radial gas flow into the deposition chamber 28. The gas ports 84 are radially and axially positioned at varying increments along the length of, and/or around, the reaction chamber 14 to evenly distribute the flow of gas into the reaction chamber 14.

In operation, referring to FIGS. 2 and 3, induction coils 24 elevate the temperature of the chlorination chamber 26 to at least 500° C. Chlorine gas flows upwardly from below the tantalum pot 50 and passes through the flow port 68 of the manifold 60, around the manifold 60, and through the flow ports 53 of the pot 50 to react with the heated tantalum and form tantalum chloride gas. The tantalum chloride gas exits the tantalum pot 50 via gas ports 59 of the lid 57 and enters the tubular members 82, and is subsequently redirected into the deposition chamber 28 through the gas flow ports 84. Hydrogen gas and air flow downwardly into the deposition chamber 28 through hydrogen gas input 17 and air input 19, respectively. The deposition chamber 28 is heated to at least 900° C. by induction coil 22 in order to drive the deposition reaction between hydrogen gas, air, and tantalum chloride gas. The deposition reaction results in tantalum deposition on the ligaments of the substrates 100. Gaseous hydrogen chloride forms as a byproduct and flows downwardly from the deposition chamber 28, through the flow ports 78 of the plate 40 and the center portions 54, 55, and 69 of the respective pot 50, lid 57, and manifold 60, and exits through the exhaust output 18.

Figure 9:
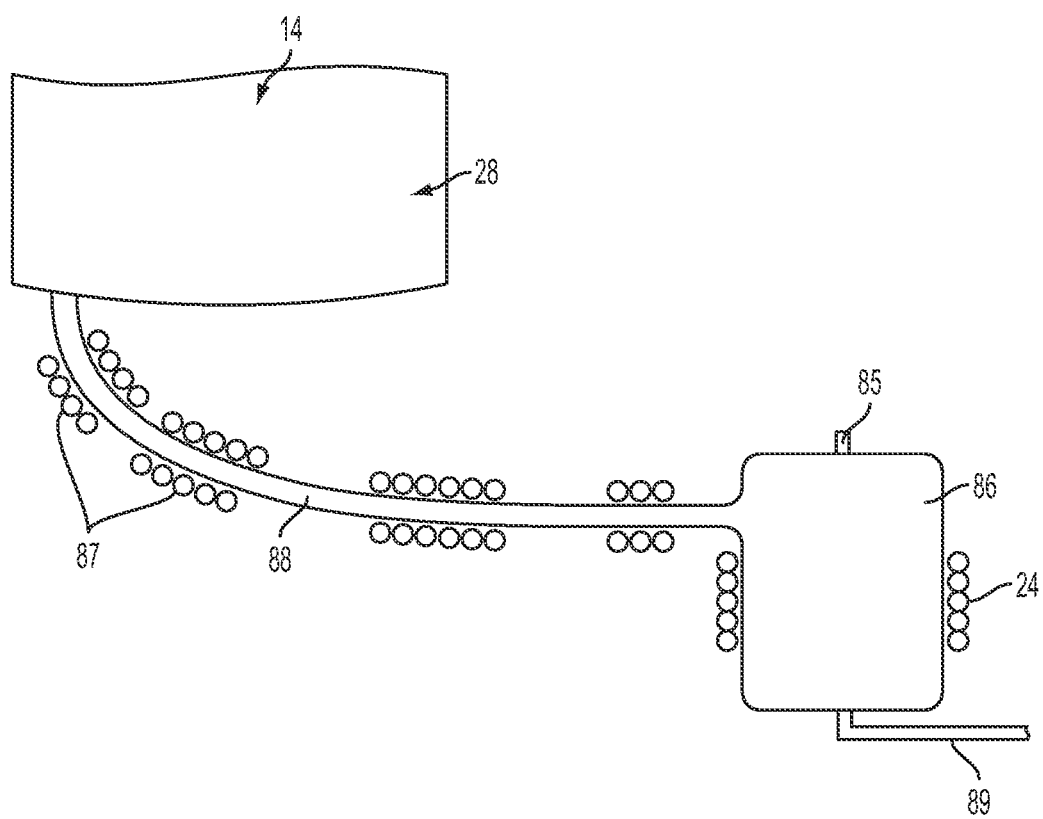
FIG. 9 is a schematic view of a portion of a CVI apparatus including an external chlorination chamber.

As is illustrated in FIG. 9, an alternative embodiment of the reaction chamber 14 includes an external chlorination chamber 86. The chlorination chamber 86 contains solid tantalum and is connected to the reaction chamber 14 by a graphite pipe 88 or other tubing device comprised of conductive material. The chlorination chamber 86 includes a gas inlet 89 that receives chlorine gas and converts the solid tantalum to tantalum chloride gas. To facilitate this reaction, a heat source, for example induction coil 24, heats the chlorination chamber 86. The graphite pipe 88 serves as an outlet for the tantalum chloride gas and provides a passageway to the deposition chamber 28. Additionally, a supplemental heat source 87, such as an induction coil or other type of heat tracing, surrounds the pipe 88 to prevent the gaseous tantalum chloride from cooling and converting the tantalum chloride gas to the solid state, and potentially clogging the pipe 88. A thermocouple 85 may be provided on the chlorination chamber 86 and/or the pipe 88 to monitor the temperatures therein.

2. Vacuum Pulsing

Figure 10:
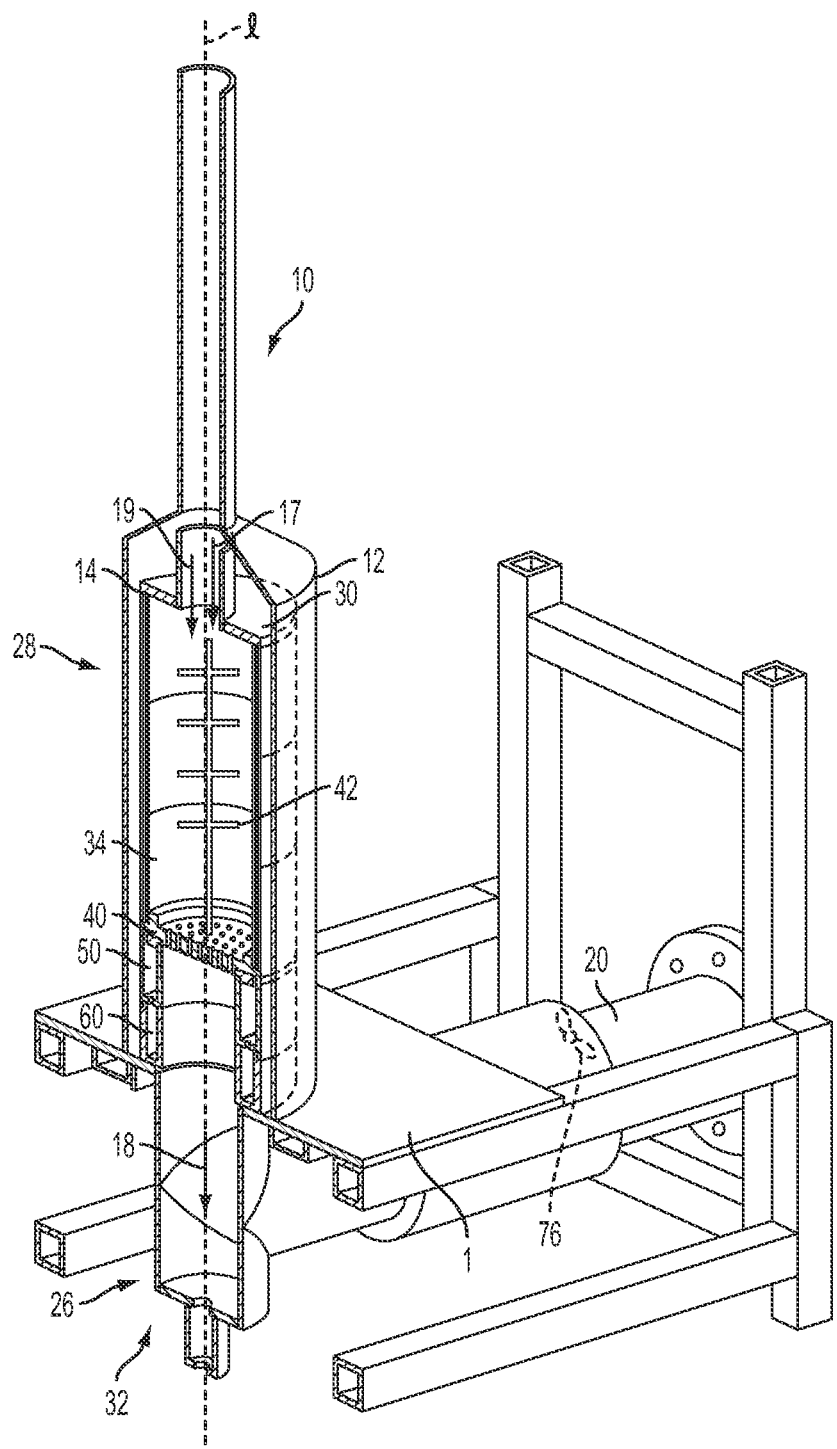
FIG. 10 is a cross-sectional view of a CVI apparatus designed with an adjustable vacuum system.

Typical CVI reaction chambers include a vacuum system that maintains a static vacuum level. Referring to FIG. 10, the improved reaction chamber 14 includes an automated vacuum system 20 that varies and/or pulses the vacuum level. The illustrative vacuum system 20 operably couples a valve 76, for example a butterfly valve, to the gas exhaust 18. The apparatus 10 may also include manual and/or electrical control means (e.g., a computerized controller) to simultaneously adjust the vacuum level applied by vacuum system 20, the position of valve 76, and/or the gas flow rates into the reaction chamber 14.

Contrary to static vacuum levels, vacuum pulsing may involve actuating valve 76 between a "closed" position to contain the gases in reaction chamber 14, and an "open" position, whereby gases exit the reaction chamber 14. Depending on the gas flow rates into the reaction chamber 14, closing the valve 76 may increase the pressure inside the reaction chamber 14. When the valve 76 is open, the vacuum system 20 is configured to remove gases from within the reaction chamber 14 via exhaust 18. The valve 76 may be opened during and after CVI cycles. When the valve 76 is closed, vacuum system 20 may become blocked or separated from the reaction chamber 14, and gases may no longer exit via exhaust 18.

By repeatedly opening and closing the valve 76, the reaction chamber 14 may be subjected to a plurality of vacuum cycles, each having a relatively high vacuum level when the valve 76 is open (e.g., 2 to 10 Torr) and a relatively low vacuum level (e.g., near atmospheric pressure or more) when the valve 76 is closed. Each vacuum cycle may be about 30 to 300 seconds in length. Also, the relatively high vacuum level may occur for about 25% to 75% of each vacuum cycle, with the relatively low vacuum level occurring during the rest of the vacuum cycle. It is also within the scope of the present disclosure that the vacuum cycle may include at least one intermediate vacuum level between the high and low vacuum levels.

The vacuum system 20 may also simultaneously stop the flow of gas into the reaction chamber 14 to allow the substrates 100 to "soak" in the process gases already contained within the deposition chamber 28. As such, the rate of the deposition reaction is maintained. However, if gas continues to flow into the deposition chamber 28 when the valve 76 is closed, the deposition rate may increase because more gases enter the deposition chamber 28 while no gases exit, which may impact the effectiveness of the CVI cycle. On the other hand, if hydrogen gas continued flowing into the deposition chamber 28 with the valve 76 closed, the hydrogen could saturate the tantalum chloride gas and prevent tantalum from depositing onto the surface of the substrates 100.

In addition to soaking the substrates 100, vacuum pulsing may increase the turbidity of the gases within the deposition chamber 28. Manipulating the gas supply and the vacuum may redirect the gases in a plurality of directions and provide a turbulent gas flow within the deposition chamber 28. Turbulence may increase the gas flow around and through the pores of the substrates 100, thereby increasing the contact between the tantalum chloride gas and the substrates 100 and further the deposition reaction.

2.1. Vacuum Pulsing Example

In order to determine the effect of vacuum pulsing on deposition efficiency and weight variance, testing was conducted on multiple substrates 100 using 10-hour CVI cycles. During each CVI cycle, the valve 76 of the apparatus 10 was oscillated between the open and closed positions in order to vary the vacuum level in the deposition chamber 28. Each vacuum pulse cycle began by opening the valve 76 to the fullest extent in order to expose the deposition chamber to a predetermined maximum vacuum level (i.e., to decrease the pressure in the deposition chamber 28). The amount of time at which the valve 76 remained in the open position varied between each vacuum pulse cycle and was calculated as a fraction of the overall time of the vacuum pulse cycle ("open fraction"). The open fraction may also be expressed as a percentage of the overall vacuum pulse cycle. Following the open fraction, the valve 76 was closed to remove the vacuum. However, the process gases continued to flow into the deposition chamber 28, which caused the pressure within the deposition chamber 28 to increase. When the pressure within the deposition chamber 28 reached a predetermined level, the gas flow was adjusted or stopped to allow "soaking" to occur. Each vacuum pulse cycle ended after substrates 100 soaked in the process gases, at which time the valve was re-opened for the next vacuum pulse cycle.

The following variables were evaluated for their impact on deposition efficiency and weight variance: the maximum vacuum level from 2 to 10 Torr; the duration of each vacuum pulse cycle from 30 to 300 seconds; and the open fraction of each vacuum pulse cycle from 0.25 (i.e., 25% of the overall vacuum pulse cycle) to 0.75 (i.e., 75% of the overall vacuum pulse cycle). With respect to deposition efficiency, the maximum vacuum level and the open fraction were found to be statistically significant. It was observed that high vacuum levels and short open fractions decreased the deposition efficiency, and therefore, increased the amount of time needed to complete the CVI process. With respect to weight variance, the duration of each vacuum pulse cycle and the open fraction were found to be statistically significant. It was observed that longer vacuum pulse cycles with shorter open fractions decreased the weight variance and contributed to a more uniform tantalum coating.

3. Gas Flow Homogenization

Figure 11:
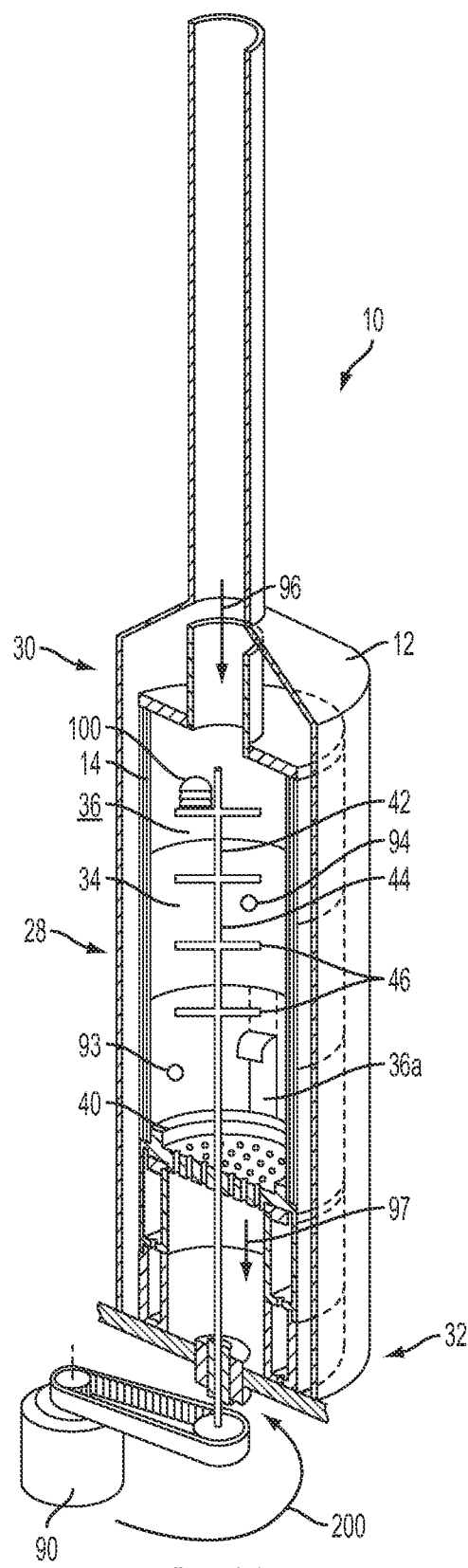
FIG. 11 is a cross-sectional view of a CVI apparatus designed to homogenize gas flow within the apparatus.

Referring to FIG. 11, the illustrative apparatus 10 may be designed to homogenize the gas flow within the deposition chamber 28. The gaseous atmosphere of the deposition chamber 28 (e.g., hydrogen, air, and tantalum chloride) typically includes a concentration gradient as a result of tantalum being continuously depleted from the atmosphere and deposited onto the substrates 100. Therefore, depending on the position of the substrates 100 along the concentration gradient, uneven tantalum deposition could potentially occur. However, the concentration gradient may be minimized by homogenizing the gases within the atmosphere of the deposition chamber 28, resulting in a more uniform deposition of tantalum onto the substrates 100. Specifically, gas flow homogenization uniformly distributes the tantalum chloride within the deposition chamber 28. Therefore, each of the substrates 100 is exposed to approximately the same amount of tantalum chloride. Factors that may affect gas flow homogenization include the flow rate of chlorine gas, the flow rate of hydrogen gas, the ratio of hydrogen to chlorine in the deposition chamber 28, and rotation of the substrates 100.

One exemplary embodiment of the apparatus 10 is illustrated in FIG. 11 and includes a motor 90 or another suitable actuator for rotating the shelving unit 42 within the deposition chamber 28. The motor 90 rotates the shelving unit 42 in a counterclockwise direction, shown at 200 in FIG. 11, or in a clockwise direction, or may alternate between such directions. The motor 90 is rotatably coupled to the post 44 of shelving unit 42 via a belt drive or gear set, for example. Rotation of the shelving unit 42 may increase the turbulence within the gaseous atmosphere of the deposition chamber 28. As such, the turbulence caused by the rotation mixes the different concentrations of tantalum chloride gas to uniformly distribute the tantalum chloride throughout the deposition chamber 28. The shelving unit 42 may be rotated at speeds as low as 2 revolutions per minute (rpm), 4 rpm, or 6 rpm, and as high as 8 rpm, 10 rpm, or more, or within any range delimited by any pair of the forgoing values.

Additionally, by rotating the shelving unit 42 within the deposition chamber 28, the substrates 100 that are stacked upon the shelving unit 42 may rotate through any localized "hot spots" 93 and "cold spots" 94 that could result from defects on the inner surface 36 of the side wall 34 of the reaction chamber 14. For example, the inner surface 36 may include nicks, scratches, dents, divots, protrusions, notches, edges or other imperfections that experience a localized temperature profile different from that of other areas of side wall 34 and/or within reaction chamber 14. The deposition reaction is affected by temperature and, therefore, rotation may consistently move the substrates 100 throughout the localized temperature profile of the deposition chamber 28 to facilitate a more uniform tantalum deposition.

Alternatively or in addition to moving the substrates 100, the gas flow within the apparatus 10 may be homogenized by adjusting the flow rates of chlorine and hydrogen into the deposition chamber 28. Chlorine gas, hydrogen gas, and other process gases may enter the deposition chamber 28 via a gas input 96 and exit the deposition chamber 28 via an exhaust outlet 97. Varying the flow rates of the process gases may shift the deposition reaction, thereby causing more tantalum to deposit on the substrates 100.

3.1. Gas Flow Homogenization Example 1

Tests were conducted to determine if rotation affected deposition efficiency and weight variance. The speed at which the substrates 100 were rotated within the deposition chamber 28 varied between 0 and 10 rpm. Rotating the substrates 100 within the deposition chamber 28 decreased the weight variance; however, the rotation did not affect the deposition efficiency. By using rotation to increase the turbidity of the process gases and/or move the substrates 100 between localized hot spots 93 and cold spots 94, a more uniform tantalum coating may be deposited onto the substrates 100. Also, the plate 40 may be configured to rotate, translate, oscillate, and move in other various ways to achieve the effect of the rotation detailed above with respect to the shelving unit 42.

3.2. Gas Flow Homogenization Example 2

Testing was conducted on multiple substrates 100 using 10-hour CVI cycles in order to quantify the effect of variable gas flow rates on the deposition efficiency and weight variance. In particular, gas flow homogenization was tested by varying the chlorine flow rate and the ratio of hydrogen to chlorine. The chlorine gas flow rate was varied between 600 and 1000 standard cubic centimeters per minute (sccm) and the hydrogen gas flow rate was varied between 600 and 3000 sccm. Using various combinations of the flow rates delimited by the foregoing values, the ratio of hydrogen gas to chlorine gas was adjusted between 1:1 and 3:1.

The results of these tests determined that increasing the ratio of hydrogen to chlorine from 1:1 to 3:1 increased the deposition efficiency. Likewise, the deposition efficiency increased when the chlorine gas flow rate was decreased from 1000 sccm to 600 sccm. Therefore, the flow rates and ratio of the process gases positively affected the deposition efficiency. Conversely, when the ratio of hydrogen to chlorine was increased, with the chlorine gas flowing at a rate of 600 sccm, the weight variance increased.

4. Temperature Uniformity

As is illustrated in FIG. 1, a typical CVI reaction chamber is heated, via induction, to approximately 900° C. with an induction coil in order to drive the deposition reaction. However, the location of the induction coil may affect the temperature profile of the reaction chamber and the deposition reaction. Specifically, the induction coils may induce excess radiant heat to areas of the deposition chamber, which results in a non-uniform temperature profile within the reaction chamber.

Figure 12:
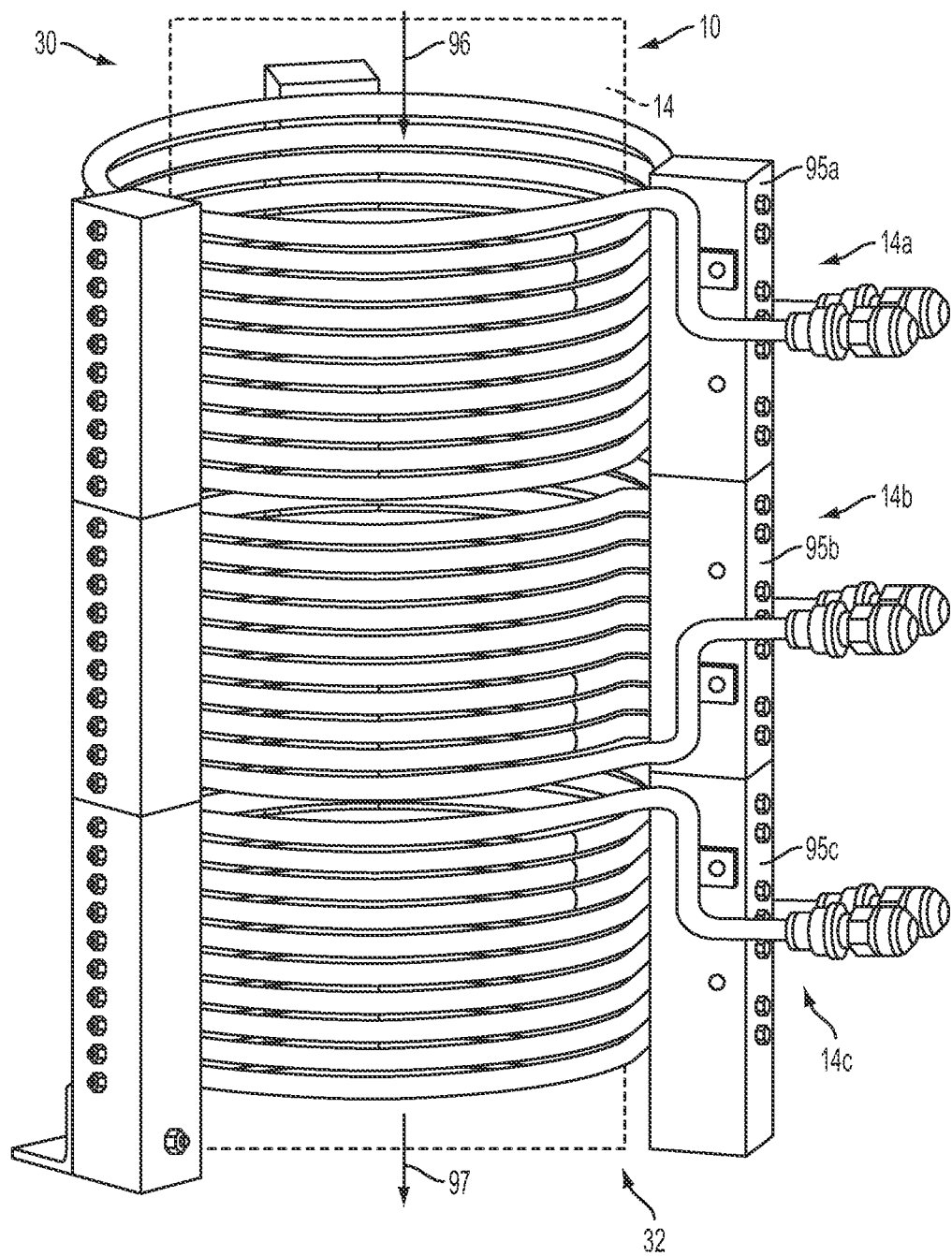
FIG. 12 is a front perspective view of three independent heating coils surrounding a CVI apparatus.

With reference to FIG. 12, the improved CVI reaction chamber 14 includes gas inlet 96 at the upper end 30 of the reaction chamber 14 and exhaust outlet 97 at the lower end 32. As gases, such as tantalum chloride, hydrogen, and air, flow downwardly through the reaction chamber 14, a decreasing concentration gradient forms with respect to the amount of tantalum chloride present in the deposition chamber 28. When the process gases, including tantalum chloride, enter the reaction chamber 14 from the upper end 30, the concentration of tantalum chloride is greater near the upper end 30 than near the lower end 32; therefore, the concentration of tantalum chloride decreases in the direction of gas flow. The concentration gradient may form because the gaseous tantalum chloride reacts to deposit tantalum onto the substrates 100 located near the upper end 30 before reaching substrates 100 located near the lower end 32. As such, the substrates 100 positioned near the lower end 32 of the reaction chamber 14 may receive less tantalum deposition.

To improve the CVI process, the illustrative reaction chamber 14 includes a plurality of independent coils, illustratively three induction coils 95a, 95b, 95c, in a stacked arrangement along the longitudinal length of the reaction chamber 14. Coils 95a, 95b, 95c each include approximately ten windings that are concentrated around a particular region of the reaction chamber 14. Illustratively, first coils 95a are positioned around an upper region 14a of the reaction chamber 14 near the upper end 30, second coils 95b are positioned around a middle region 14b of the reaction chamber 14, and third coils 95c are positioned around a lower region 14c of the reaction chamber 14 near the lower end 32. Each of the coils 95a, 95b, 95c is independently controlled in order to selectively vary the temperature in the respective upper, middle, and lower regions 14a, 14b, 14c of the reaction chamber 14.

In order to increase deposition efficiency, despite the decreasing concentration gradient of tantalum, the first coil 95a, the second coil 95b, and third coil 95c are used to provide a temperature profile within the reaction chamber 14, in which the temperature increases in the direction of gas flow (i.e., in the downward direction). Therefore, the temperature in the lower region 14c of the reaction chamber 14 is greater than the temperature in the upper and middle regions 14a, 14b of the chamber 14. Since temperature is a key variable for the deposition reaction, more tantalum may deposit onto the substrates 100 in regions with increased temperature. As such, the elevated temperature in the lower region 14c of the illustrative reaction chamber 14 may compensate for the decreased concentration of tantalum in the lower region 14c and drive the deposition reaction.

4.1. Temperature Uniformity Example

Tests were conducted to quantify the effect of the temperature profile on deposition efficiency and weight variance. Induction coils 95a, 95b, 95c were used to create descending, ascending, and uniform temperature profiles within the reaction chamber 14. The descending profile varied the temperature of the reaction chamber 14 between approximately 1050° C. near the upper end 30 and approximately 900° C. near the lower end 32. Conversely, the ascending temperature profile heated the upper end 30 of the reaction chamber 14 to approximately 900° C. and the lower end 32 to approximately 1050° C. The uniform temperature profile maintained the temperature in each region 14a, 14b, 14c of the reaction chamber 14 at approximately 925° C. Using these temperature profiles, CVI cycles were conducted on multiple substrates 100 for approximately 10 hours. Thermocouples (not shown) were positioned within the reaction chamber 14, each corresponding to one of the induction coils 95a, 95b, 95c, in order to monitor the temperature profile during these tests.

Using the uniform temperature profile as a baseline or "control", it was observed that the ascending temperature profile affected the deposition efficiency but did not affect the weight variance in a statistically significant way. In particular, the ascending temperature profile increased the deposition efficiency, thereby decreasing the overall amount of time needed to form a porous tantalum implant. However, the descending temperature profile affected both the deposition efficiency and the weight variance. Specifically, the descending temperature profile decreased the deposition efficiency and increased the weight variance, thereby increasing the overall amount of time needed to form a porous tantalum implant.

5. Rapid Cooling

The CVI cycle occurs at a temperature of at least 900° C. and, therefore, known CVI devices may take several hours to sufficiently cool the deposition chamber 28 in order to remove the substrates 100. The overall amount of time needed to produce porous tantalum implants may be reduced by decreasing the cooling period of a CVI cycle. Furthermore, the configuration and position of the heat source affects the cooling time. However, rapidly cooling, or quenching, the substrates 100 may adversely affect the chemical and mechanical properties of the implants.

Figure 13A:
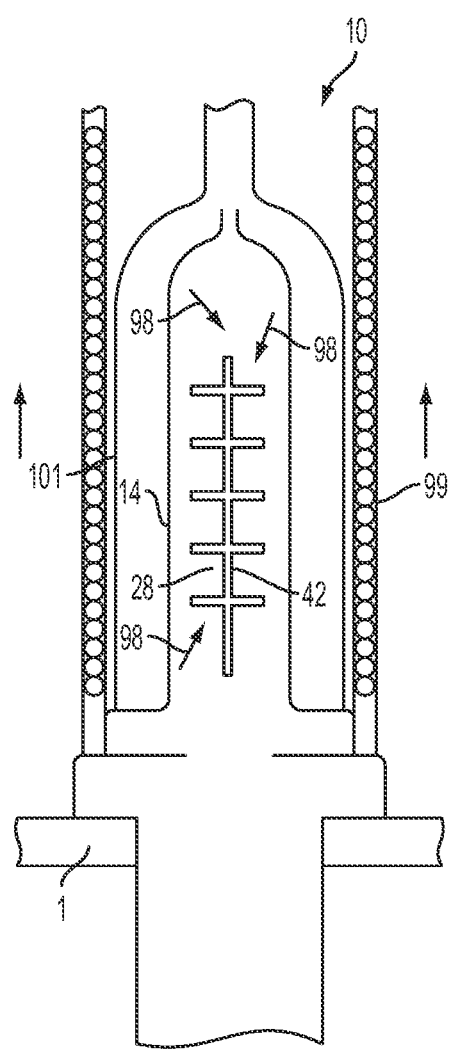
FIGS. 13A and 13B are cross-sectional views of a CVI apparatus designed to rapidly cool an internal reaction chamber of the apparatus.
Figure 13B:
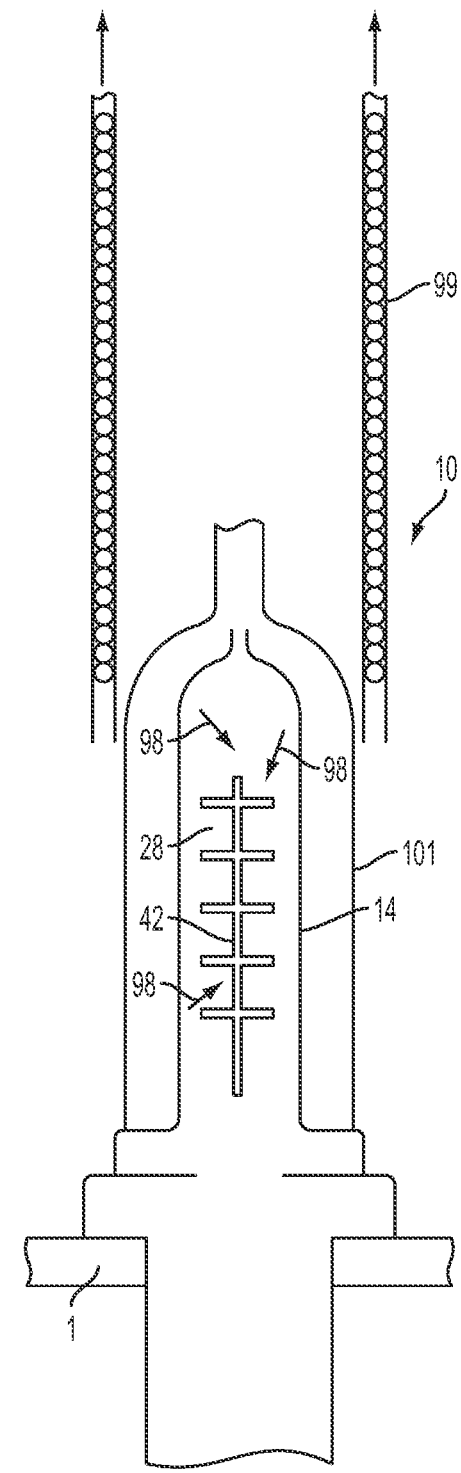

Referring to FIG. 13, an illustrative embodiment of the reaction chamber 14 is configured to rapidly cool the deposition chamber 28 after completion of a CVI cycle. Illustratively, the reaction chamber 14 includes a supply of argon gas 98 that may be injected into the reaction chamber 14 following a CVI cycle. Argon boils at approximately −186° C. (−303° F.) and, therefore, is a cold gas at room temperature. As such, argon gas 98 may be used to cool the reaction chamber 14. The flow rate of argon gas 98 may be as low as approximately 500, 1000, or 1500 sccm, and as high as approximately 8,000, 9,000, or 10,000 sccm, or within any range delimited by any pair of the foregoing values. Additionally, the argon gas 98 may be held under a vacuum level as low as approximately 0, 2, or 4 Torr or as high as approximately 6, 8, or 10 Torr, or within any range delimited by any pair of the foregoing values. However, if a heat source is positioned around the reaction chamber 14 during the cooling period, the flush of argon gas 98 is potentially less effective.

Therefore, the illustrative embodiment of the reaction chamber 14 may further include a removable induction coil 99 positioned around a vacuum chamber 101 and the reaction chamber 14. The removable induction coil 99 may be removed from the reaction chamber 14 through pneumatic, hydraulic, or automatic means. Illustratively, the removable induction coil 99 is lifted from the reaction chamber 14 and is stored at a position above the reaction chamber 14. The vacuum chamber 101 is intermediate the induction coil 99 and the reaction chamber 14 and continues to surround the reaction chamber 14 after the induction coil 99 is removed in order to facilitate the flow of argon gas 98 and, therefore, the cooling process. The simultaneous removal of heat and the flush of argon gas 98, under vacuum, provide maximum cooling potential.

5.1. Rapid Cooling Example

Following a series of CVI cycles, tests were conducted to determine if the chemical and mechanical properties of the porous tantalum substrates 100 were affected by the rapid cooling period. After the deposition reaction occurred, the CVI apparatus, including the induction coil 99 and the gas supplies, was turned off and the induction coil 99 was removed. At the same time, varying levels of argon gas 98, held under vacuum, were supplied to the reaction chamber 14. The tests varied the flow rate of the argon gas 98 from 500 to 10,000 sccm. Additionally, the argon gas 98 was held under vacuum form 0 to 10 Torr. The cooling period was concluded when the temperature of the reaction chamber 14 reached 125° C.

Cooling period time and the chemical and mechanical properties of the substrates 100 were the outputs used to quantify these tests. The level of vacuum and the flow rate of the argon gas 98 were statistically significant factors for rapid cooling. Shorter cooling periods were observed when the flow rate of argon gas 98 was increased and combined with a low level of vacuum. For example, the tests indicated that when the flow rate of argon gas 98 was 5,000 sccm, held under vacuum at a pressure of approximately 10 Torr, the cooling period was reduced from approximately 340 minutes to approximately 260 minutes. It also was observed that the rapid cooling process did not adversely affect the chemical and mechanical properties of the porous tantalum substrates 100. Following the rapid cooling period, the ultimate compressive strength, the specific compressive strength, the ductility, and the chemical properties of the substrates 100 were analyzed and determined to be acceptable.

6. Self-Cleaning Furnace

The above-described furnace configurations may be configured to self-clean. During a CVI cycle, tantalum builds up on the inner surface 36 of the side wall 34 of the reaction chamber 14. Typically, the tantalum build-up is removed by manually disassembling the apparatus 10 and using acidic or caustic stripping agents such as hydrofluoric acid. However, the illustrative reaction chamber 14 may implement a chlorine stripping process, whereby the reaction chamber 14 is heated and chlorine gas is injected into the reaction chamber 14 to react with the solid tantalum build-up and convert the tantalum to tantalum chloride gas, which may be exhausted from the reaction chamber 14.

The chlorine stripping gas may be injected directly into the deposition chamber 28 to clean the inner surface 36 of the side wall 34 via gas input 96 (FIG. 11) or another suitable gas input. However, it is also within the scope of the present disclosure that the chlorine stripping gas may first be injected into chlorination chamber 26 via chlorine gas input 16 (FIG. 2) before reaching deposition chamber 28. If the chlorine stripping gas will travel through the chlorination chamber 26, any loose tantalum nuggets or scraps in the pot 50 may be removed manually (e.g., by dumping the pot 50) to avoid "wasting" the chlorine stripping gas reaction on these loose source materials. Also, the temperature of the chlorination chamber 26 may be lower during the self-cleaning cycle (e.g., less than 500° C.) than during the CVI production cycle (e.g., more than 500° C.) to avoid "wasting" the chlorine stripping gas reaction on these loose source materials.

The self-cleaning cycle may occur after a series of CVI production cycles. Any coated substrates 100 may be removed from the reaction chamber 14 before running the self-cleaning cycle to avoid "wasting" the chlorine stripping gas reaction by stripping tantalum from the coated substrates 100.

Alternatively or in addition to the chlorine stripping process, a metal or graphite foil insert or film 36a (FIG. 11) may be secured to the inner surface 36 of the side wall 34 of the reaction chamber 14, onto which tantalum may deposit during a CVI cycle. The foil insert 36a may be easily removed and replaced as desired following one or more CVI cycles. In the illustrated embodiment of FIG. 11, the foil insert 36a is shown being peeled away from the inner surface 36 of the side wall 34. The foil insert 36a may have an adhesive backing that allows for selective application and removal.

While this invention has been described as having exemplary designs, the present invention can be further modified within the spirit and scope of this disclosure. This application is therefore intended to cover any variations, uses, or adaptations of the invention using its general principles. Further, this application is intended to cover such departures from the present disclosure as come within known or customary practices in the art to which this invention pertains.

What is claimed is:

1. A method of operating a chemical vapor infiltration apparatus to produce an orthopedic implant, the method comprising the steps of:
   placing a porous substrate into a reaction chamber of the chemical vapor infiltration apparatus, the reaction chamber having a first end and a second end; and
   exposing the porous substrate to a first gas and a second gas in the reaction chamber, wherein the first gas enters the reaction chamber proximate said first end and the second gas enters the reaction chamber proximate said second end, and wherein the first gas and the second gas react in the reaction chamber to deposit a biocompatible metal onto the porous substrate.

2. The method of claim 1, wherein said porous substrate includes a reticulated vitreous carbon substrate.

3. The method of claim 1, wherein the biocompatible metal comprises tantalum, the first gas comprises tantalum chloride, and the second gas comprises hydrogen.

4. The method of claim 1, wherein, during the exposing step, the first end of the reaction chamber is controlled at a first temperature and the second end of the reaction chamber is controlled at a second temperature, the first temperature exceeding the second temperature.

5. The method of claim 1 further comprising varying a vacuum level in the reaction chamber during the exposing step.

6. The method of claim 5, wherein said varying step includes subjecting the reaction chamber to a plurality of vacuum cycles that each include decreasing the pressure in the reaction chamber and increasing the pressure in the reaction chamber.

7. The method of claim 6, wherein the plurality of vacuum cycles each include decreasing the pressure in the reaction chamber and then subsequently increasing the pressure in the reaction chamber until a predetermined pressure is reached and then maintaining said predetermined pressure for a period of time.

8. The method of claim 5, wherein the varying step comprises repeatedly exposing the reaction chamber to a vacuum system and separating the reaction chamber from the vacuum system.

9. The method of claim 1, further comprising at least one of:
   closing a first gas input into the reaction chamber during the varying step to prevent the flow of more of the first gas into the reaction chamber; and
   closing a second gas input into the reaction chamber during the varying step to prevent the flow of more of the second gas into the reaction chamber.

10. The method of claim 1 further comprising flushing the reaction chamber with argon gas.

11. A method of operating a chemical vapor infiltration apparatus to produce an orthopedic implant, the method comprising the steps of:
   placing a porous substrate into a reaction chamber of the chemical vapor infiltration apparatus, the reaction chamber having a top portion and a bottom portion; and
   exposing the porous substrate to a first gas and a second gas in the reaction chamber, wherein the first gas and the second gas react in the reaction chamber to deposit a biocompatible metal onto the porous substrate,
   wherein said exposing step includes the first gas flowing upwardly into the reaction chamber and the second gas flowing downwardly into the reaction chamber.

12. The method of claim 11, wherein said porous substrate includes a reticulated vitreous carbon substrate.

13. The method of claim 11, wherein, during the exposing step, the bottom portion of the reaction chamber is controlled at a first temperature and the top portion of the reaction chamber is controlled at a second temperature, the first temperature exceeding the second temperature.

14. The method of claim 11 further comprising varying a vacuum level in the reaction chamber during the exposing step.

15. The method of claim 14, wherein said varying step includes subjecting the reaction chamber to a plurality of vacuum cycles that each include decreasing the pressure in the reaction chamber and increasing the pressure in the reaction chamber.

16. The method of claim 15, wherein the plurality of vacuum cycles each include decreasing the pressure in the reaction chamber and then subsequently increasing the pressure in the reaction chamber until a predetermined pressure is reached and then maintaining said predetermined pressure for a period of time.

17. The method of claim 14, wherein the varying step comprises operating the reaction chamber in a plurality of vacuum cycles, each vacuum cycle having a relatively high vacuum level and a relatively low vacuum level.

18. The method of claim 11, further comprising at least one of:
closing a first gas input into the reaction chamber during the varying step to prevent the flow of more of the first gas into the reaction chamber; and
closing a second gas input into the reaction chamber during the varying step to prevent the flow of more of the second gas into the reaction chamber.

19. The method of claim 11 further comprising flushing the reaction chamber with argon gas.

20. A method of operating a chemical vapor infiltration apparatus to produce an orthopedic implant, the method comprising the steps of:
placing a porous substrate into a reaction chamber of the chemical vapor infiltration apparatus; and
exposing the porous substrate to a first gas and a second gas in the reaction chamber, wherein the first gas and the second gas react in the reaction chamber to deposit a biocompatible metal onto the porous substrate,
wherein said exposing step includes the first gas flowing into the reaction chamber in a first direction and the second gas flowing into the reaction chamber in a second direction opposing said first direction.

21. The method of claim 20, wherein said porous substrate includes a reticulated vitreous carbon substrate.

22. The method of claim 20 further comprising varying a vacuum level in the reaction chamber during the exposing step.

23. The method of claim 22, wherein said varying step includes subjecting the reaction chamber to a plurality of vacuum cycles that each include decreasing the pressure in the reaction chamber and increasing the pressure in the reaction chamber.

24. The method of claim 23, wherein the plurality of vacuum cycles each include decreasing the pressure in the reaction chamber and then subsequently increasing the pressure in the reaction chamber until a predetermined pressure is reached and then maintaining said predetermined pressure for a period of time.

25. The method of claim 20, further comprising at least one of:
closing a first gas input into the reaction chamber during the varying step to prevent the flow of more of the first gas into the reaction chamber; and
closing a second gas input into the reaction chamber during the varying step to prevent the flow of more of the second gas into the reaction chamber.

* * * * *